United States Patent
Matsuki et al.

(10) Patent No.: US 7,511,905 B2
(45) Date of Patent: Mar. 31, 2009

(54) MAGNETIC COUPLED ACTUATOR

(75) Inventors: Kaoru Matsuki, Kawasaki (JP); You Kondoh, Yamato (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/031,906

(22) Filed: Feb. 15, 2008

(65) Prior Publication Data
US 2008/0212212 A1  Sep. 4, 2008

(30) Foreign Application Priority Data
Feb. 15, 2007  (JP) .............................. 2007-034249

(51) Int. Cl.
*G02B 7/02*  (2006.01)
*G02B 15/14*  (2006.01)

(52) U.S. Cl. ...................... 359/824; 359/814; 359/694; 359/696; 600/112

(58) Field of Classification Search ................ 359/814, 359/823, 824, 694–698; 396/55, 75, 469; 600/112; 348/208.11, 208.12; 310/13, 15, 310/49 R, 114, 257; 324/207.2, 207.21, 324/207.24; 369/44.14–44.16
See application file for complete search history.

(56) References Cited

U.S. PATENT DOCUMENTS

| | | | | |
|---|---|---|---|---|
| 5,289,318 A | * | 2/1994 | Sekine et al. ............... | 359/813 |
| 5,359,992 A | * | 11/1994 | Hori et al. ....................... | 126/4 |
| 5,572,372 A | * | 11/1996 | Sekine et al. ............... | 359/824 |
| 5,602,808 A | * | 2/1997 | Futagawa et al. ......... | 369/44.14 |
| 6,522,477 B2 | * | 2/2003 | Anhalt ....................... | 359/694 |
| 6,633,438 B2 | * | 10/2003 | Anhalt ....................... | 359/694 |
| 6,856,469 B2 | * | 2/2005 | Yoneyama et al. .......... | 359/696 |
| 7,440,201 B2 | * | 10/2008 | Tsuruta et al. .............. | 359/824 |

FOREIGN PATENT DOCUMENTS

JP  2004-129950  4/2004

* cited by examiner

*Primary Examiner*—Loha Ben
(74) *Attorney, Agent, or Firm*—Scully, Scott, Murphy & Presser, P.C.

(57) ABSTRACT

A magnetic coupled actuator includes a lens which is movable in an optical axis direction AX, a lens frame which is coupled with the lens, a lens barrel which seals and accommodates the movable lens and the lens frame to be airtight, a permanent magnet which is disposed at an outer side of the lens barrel, facing the lens frame, and is disposed to be movable in the optical axis AX direction, and a wire of which, one end is coupled with the permanent magnet, and which moves the permanent magnet in the optical axis AX direction. At least one of the lens frame and the permanent magnet is a magnetic field generating means.

6 Claims, 3 Drawing Sheets

MAGNETIC COUPLED ACTUATOR

CROSS-REFERENCE TO RELATED APPLICATION

The present application is based upon and claims the benefit of priority from the prior Japanese Patent Application No. 2007-034249 filed on Feb. 15, 2007; the entire contents of which are incorporated herein by reference.

BACKGROUND OF THE INVENTION

1. Field of the Invention

The present invention relates to an actuator, and particularly, to an actuator which is driven by using magnetism.

2. Description of the Related Art

An optical system having a focusing and a zooming function, has hitherto required a mechanism for moving a lens in a lens barrel in an optical axis direction. As a mechanism for moving the lens, for example, a mechanism which moves the lens by controlling passing of electricity to an actuator which has been installed in an endoscope has been proposed, As an example of such mechanism, an image pickup apparatus for an endoscope shown in Japanese Patent Application Laid-open Publication No. 2004-129950 has been proposed.

FIG. 3 shows a cross-sectional view of a structure according to a conventional technology. Inside an image pickup element frame 20, shape memory alloys 27 and 28 as driving means (actuators) of which, an entire length is extended due to heating by passing electricity are provided. An interior of a shell 19, and an image pickup optical frame 18, and the image pickup element frame 20 are connected by the shape memory alloys 27 and 28.

Based on a pressing operation of an operating section 29, a contact point 30 is put ON/OFF and electricity is passed and stopped. Accordingly, it is possible to adjust a supply of an electric current for heating, to the shape memory alloys 27 and 28. As a result of this, it is possible to change relative positions of the image pickup optical frame 18 and the image pickup element frame 20.

However, an amount of displacement of the actuator is restricted according to a length of the shape memory alloy. Therefore, an amount of displacement of the actuator which is disposed at an interior of a hard portion of an endoscope becomes small. Consequently, it is not possible to make substantial an amount of lens movement. Accordingly, a degree of freedom of optical designing becomes low.

Moreover, in the endoscope, airtightness of a structure including a structure of a surrounding of an image pickup apparatus and a surrounding of the actuator has been sought from a point of view of cleaning etc. It is desirable that the airtightness is as high as possible.

SUMMARY OF THE INVENTION

The present invention is made in view of the abovementioned circumstances, and an object of the present invention is to provide a magnetic coupled actuator having a high degree of freedom of designing for an optical system which is driven, which is capable of improving an airtightness of a surrounding of an image pickup apparatus.

To solve the abovementioned issues, and to achieve the object, according to the present invention, there can be provided a magnetic coupled actuator including a movable lens which is movable in an optical axis direction, a first magnetic body which is coupled with the movable lens, a lens barrel which seals and accommodates the movable lens and the first magnetic body to be airtight, a second magnetic body which is disposed at an outer side of the lens barrel, facing the first magnetic body, and which is disposed to be movable in the optical axis direction, and a wire member of which, one end is coupled with the second magnetic body, and which moves the second magnetic body in the optical axis direction, and at least one of the first magnetic body and the second magnetic body is a magnetic field generating means.

Moreover, according to a preferable aspect of the present invention, it is desirable that the magnetic field generating means is a permanent magnet.

Moreover, according to a preferable aspect of the present invention, it is desirable that a first position regulating member and a second position regulating member are disposed inside the lens barrel, and a displacement of the movable lens is restricted between the first position regulating member and the second position regulating member, by a mechanical constraint.

Moreover, according to a preferable aspect of the present invention, it is desirable that the wire member is made of a shape memory alloy wire.

Moreover, according to a preferable aspect of the present invention, it is desirable that the magnetic coupled actuator further includes a tube member which can be bent, and which includes the shape memory alloy wire, and one end of the tube member is fixed to the lens barrel, and the other end of the tube member is fixed to one end of the shape memory alloy wire which is not fixed to the second magnetic body, and a drive mechanism which is structured such that a relative position of one end of the tube member which is fixed to the second magnetic body and the lens barrel changes due to an expansion and a contraction of the shape memory alloy wire.

Moreover, according to a preferable aspect of the present invention, it is desirable that the drive mechanism has an elastic body for bias such that a force is exerted in a direction in which the relative position of one end of the tube member which is fixed to the second magnetic body and the lens barrel changes, and in a reverse direction thereof, due to the expansion and the contraction of the shape memory alloy wire.

DETAILED DESCRIPTION OF THE PREFERRED EMBODIMENTS

Exemplary embodiments of a magnetic coupled actuator according to the present invention will be described below in detail by referring to the accompanying diagrams. However, the present invention is not restricted to the embodiments described below.

First Embodiment

Figure 1:
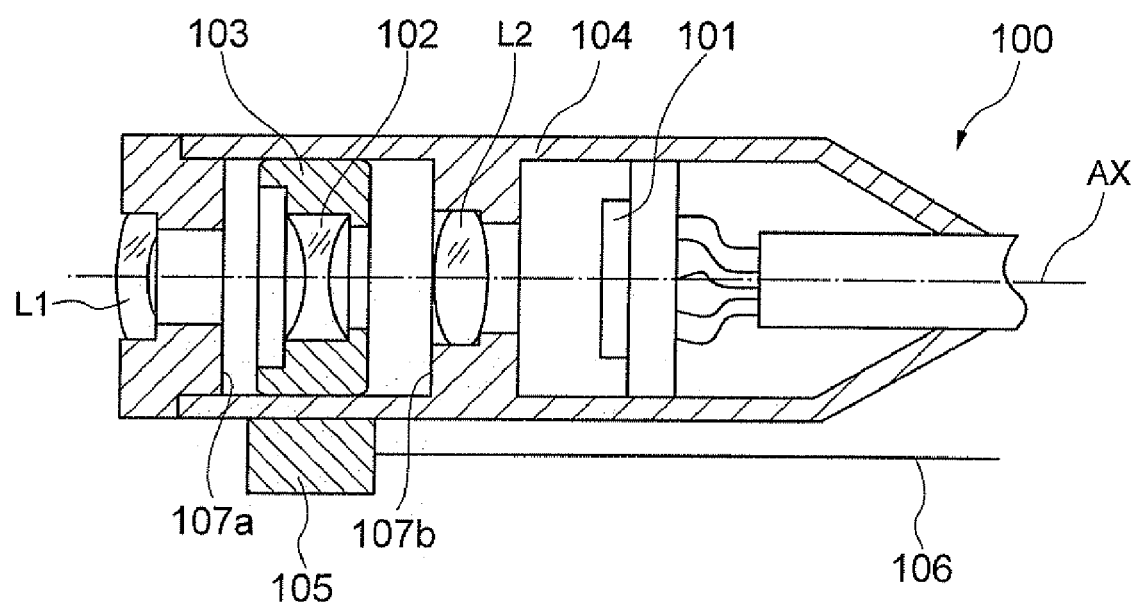
FIG. 1 is a diagram showing a schematic structure of a magnetic coupled actuator according to a first embodiment of the present invention.

FIG. 1 is a diagram showing a cross-sectional view of a magnetic coupled actuator 100 according to a first embodiment of the present invention. The first embodiment is an embodiment in which the magnetic coupled actuator 100 is used in a front end portion of an endoscope.

A lens frame 103 which holds a lens 102 is formed by a first magnetic body which is made of a material such as iron and stainless steel. Moreover, fixed lenses L1 and L2 are provided along an optical axis AX. An image of an object (not shown in the diagram) is formed on an image pickup surface of an image pickup element 101 via the lenses L1, L2, and 102. The lens 102 corresponds to a movable lens. Moreover, by moving the lens 102 along the optical axis AX, it is possible to carry out focusing and zooming.

The lens frame 103 accommodates a lens barrel 104. The lens frame 103 is disposed to be movable in an optical axis AX direction inside a space shown in FIG. 1. A permanent magnet 105 is disposed at an outer side of the lens barrel 104, facing the lens frame 103. The permanent magnet 105 corresponds to a second magnetic body and a magnetic field generating means.

The lens frame 103 and the permanent magnet 105 are subjected to magnetic coupling via the lens barrel 104. At one end of the permanent magnet 105, a wire 106 is extended in the optical axis AX direction. By pulling or pushing the wire 106 from an outside, the permanent magnet 105 can be moved in the optical axis direction. Accordingly, the lens frame 103 which is subjected to the magnetic coupling with the permanent magnet 105 can be moved inside the lens barrel 104.

In the first embodiment, the lens frame 103 is let to be one magnetic body and the permanent magnet 105 is let to be the other magnetic body. However, without restricting to this, the lens frame 103 may be formed by a permanent magnet and a portion of the permanent magnet 105 may be formed by a magnetic body, Moreover, both the lens frame 103 and the permanent magnet 105 may be permanent magnets.

Generally, in a case of moving a lens frame which holds a lens provided inside a lens barrel in the optical axis direction, the lens frame and a member provided on an outer side of the lens barrel, which moves the lens frame are connected mechanically, and it is necessary to form a groove or a hole in the lens barrel 104.

However, since the lens frame 103 and the permanent magnet 105 provided on the outer side of the lens barrel 104 in the first embodiment are subjected to the magnetic coupling via the lens barrel 104, and are not connected mechanically, it is not necessary to form a hole or a groove in the lens barrel 104. Therefore, it is possible to secure even higher airtightness in the lens barrel 104, together with the lenses L1 and L2 in addition to the lens 102. In the structure of the first embodiment, an environment resistance of an optical system may be improved, and may withstand an environment such as of wet sterilization at a high temperature and a high pressure.

Moreover, in the present embodiment, an amount of movement of the permanent magnet 105 is not restricted in particular. Whereas, the movement of the lens 102 is limited by regulating portions 107a and 107b. By restricting the movement of the lens 102 by these regulating portions 107a and 107b, a position of the permanent magnet 105 in the optical axis AX direction is not required to be determined accurately. In other words, the positioning of the movable lens is possible irrespective of the accuracy of movement of the permanent magnet 105.

Further, it is also possible to form the wire 106 by a shape memory alloy wire which expands and contracts by heating by passing electricity. Accordingly, it is possible to move the permanent magnet 105 by the expansion and the contraction of the shape memory alloy wire by an operation of passing electricity from an outside. Therefore, operability is improved as compared in an operation of pushing and pulling the wire 106.

Second Embodiment

Figure 2:
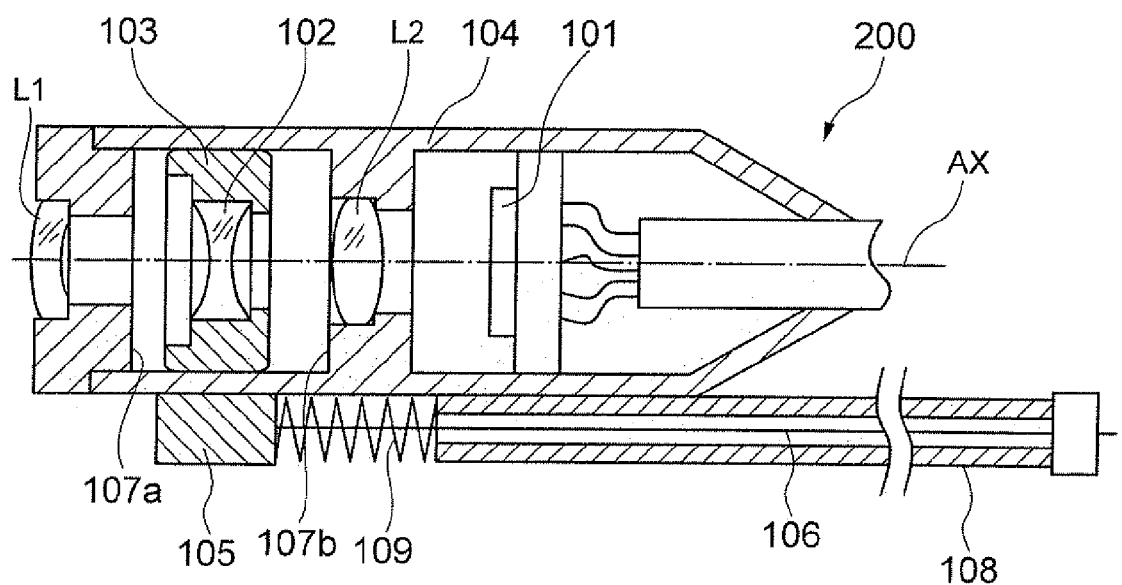
FIG. 2 is a diagram showing a schematic structure of a magnetic coupled actuator according to a second embodiment of the present invention.
Figure 3:
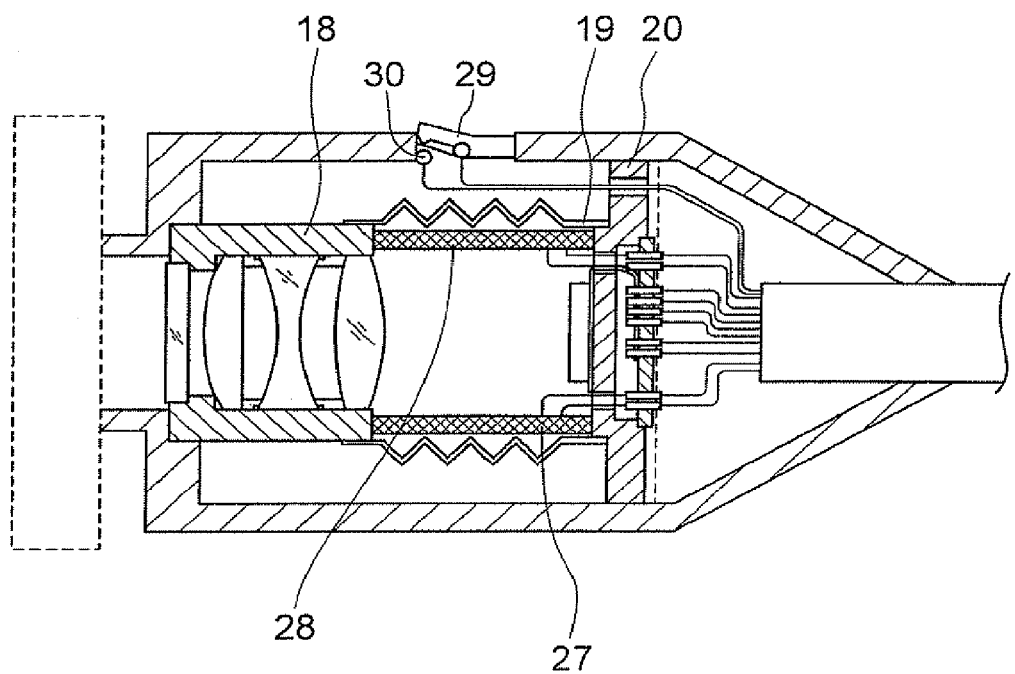
FIG. 3 is a diagram showing a cross-sectional view of a conventional endoscope apparatus.

Next, a magnetic coupled actuator 200 according to a second embodiment of the present invention will be described below. FIG. 2 shows a cross-sectional view of the magnetic coupled actuator 200 of the second embodiment. Same reference numerals are assigned to components which are same as in the first embodiment, and the description to be repeated is omitted.

In the second embodiment, a tube 108 which can be bent, which includes the shape memory alloy wire 106 is disposed. One end of the tube 108 is fixed to the lens barrel 104, and an end on the opposite side is connected to the shape memory alloy wire 106.

By connecting an end of the tube 108 which is not fixed, to one end of the shape memory alloy wire 106, the magnetic coupled actuator 200 becomes long and ductile. Therefore, it is possible to make substantial the amount of movement of the lens 102. Moreover, it is also possible to accommodate the magnetic coupled actuator 200 at a site inside an endoscope, where it can be bent.

An amount of expansion and contraction of the shape memory alloy wire 106 is determined by a length of the shape memory alloy wire 106. Therefore, when the structure is made as in the second embodiment, it is possible to dispose the shape memory alloy wire 106 to be long, and to make substantial the amount of movement of the lens 102.

In the second embodiment, the shape memory alloy wire 106 is contracted by heating by passing electricity to the shape memory alloy wire 106, and the permanent magnet 105 moves toward the image pickup element 101. At this time, a bias spring 109 exerting a force in a direction opposite to a direction of movement of the permanent magnet 105 is disposed between the permanent magnet 105 and the tube 108. Accordingly, it is possible to accelerate an elongation rate (regression speed) of the shape memory alloy wire 106 after the heating by passing electricity has been stopped. The bias spring 109 corresponds to an elastic body for bias.

As it has been described above, in each embodiment, the second magnetic body, for example, the permanent magnet 105 is moved by pulling the wire or by the wire being deformed. Accordingly, it is possible to move the first magnetic body subjected to magnetic coupling, and the lens which is supported by the first magnetic body. Here, the wire is not restricted to an SMA (shape memory alloy) wire, and the structure may be such that the wire is pulled by a motor etc. from the outside.

Moreover, by using the permanent magnet, wiring is unnecessary unlike in a case of using an electromagnet, and an assembling becomes easy and the structure becomes simple. Further, by forming the wire by a shape memory alloy, a driving force necessary at the time of moving the lens is small as compared to a structure in which the wire is pushed and pulled from the outside, and the operability is improved.

Moreover, the permanent magnet 105 is provided at an outer side of the lens barrel 104. Therefore, it is possible to make small an airtight space inside the lens barrel 104. Furthermore, as it has been mentioned above, it is not necessary to connect mechanically the permanent magnet 105 and the lens frame 103, Therefore, a hole etc. may not be formed in the lens barrel 104. As a result, the airtightness can be improved further.

Furthermore, by the permanent magnet 105 being formed on the outer side of the lens barrel 104, there is no restriction on the amount of movement of the permanent magnet 105. Accordingly, a range in which the lens 102 can move becomes wide. Accordingly, a degree of freedom of designing the lens for carrying out focusing and zooming becomes high. Moreover, an optical design for letting a depth of focus to be predetermined value becomes easy. In this manner, by making substantial the amount movement of the lens, it is possible to facilitate strengthening of focusing and a magnified observation function.

The present invention can take various modified embodiments which fairly fall within the basic teaching herein set forth.

As it has been described above, the magnetic coupled actuator according to the present invention is suitable for an endoscope for example.

According to the present invention, an effect is shown that it is possible to provide a magnetic coupled actuator having a high degree of freedom of designing for an optical system which is driven, which is capable of improving an airtightness of a surrounding of an image pickup apparatus.

What is claimed is:

1. A magnetic coupled actuator comprising:
   a movable lens which is movable in an optical axis direction;
   a first magnetic body which is coupled with the movable lens;
   a lens barrel which seals and accommodates the movable lens and the first magnetic body to be airtight;
   a second magnetic body which is disposed at an outer side of the lens barrel, facing the first magnetic body, and which is disposed to be movable in the optical axis direction; and
   a wire member of which, one end is coupled with the second magnetic body, and which moves the second magnetic body in the optical axis direction, wherein
   at least one of the first magnetic body and the second magnetic body is a magnetic field generating means.

2. The magnetic coupled actuator according to claim 1, wherein the magnetic field generating means is a permanent magnet.

3. The magnetic coupled actuator according to claim 1, wherein
   a first position regulating member and a second position regulating member are disposed inside the lens barrel, and
   a displacement of the movable lens is restricted between the first position regulating member and the second position regulating member by a mechanical constraint.

4. The magnetic coupled actuator according to claim 1, wherein the wire member is made of a shape memory alloy wire.

5. The magnetic coupled actuator according to claim 4, further comprising:
   a tube member which can be bent and which includes the shape memory alloy wire, and one end of the tube member is fixed to the lens barrel, and the other end of the tube member is fixed to one end of the shape memory alloy wire which is not fixed to the second magnetic body; and
   a drive mechanism which is structured such that a relative position between one end of the tube member which is fixed to the lens barrel and the second magnetic body changes due to an expansion and a contraction of the shape memory alloy wire.

6. The magnetic coupled actuator according to claim 5, wherein the drive mechanism has an elastic body for bias such that a force is exerted in a reverse direction against a direction in which the relative position between one end of the tube member which is fixed to the lens barrel and the second magnetic body changes due to the expansion and the contraction of the shape memory alloy wire.

* * * * *